United States Patent
Cooper et al.

(10) Patent No.: US 9,417,215 B2
(45) Date of Patent: Aug. 16, 2016

(54) VIBRATION MONITORING SYSTEM AND METHOD

(71) Applicant: GENERAL ELECTRIC COMPANY, Schenectady, NY (US)

(72) Inventors: Jared Klineman Cooper, Melbourne, FL (US); Nick David Nagrodsky, Melbourne, FL (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/501,177

(22) Filed: Sep. 30, 2014

(65) Prior Publication Data
US 2016/0091465 A1    Mar. 31, 2016

(51) Int. Cl.
*G01N 21/00* (2006.01)
*G01N 29/24* (2006.01)
*G01M 11/00* (2006.01)

(52) U.S. Cl.
CPC ........... *G01N 29/2418* (2013.01); *G01M 11/30* (2013.01); *G01N 2291/01* (2013.01)

(58) Field of Classification Search
CPC .......... G01M 11/3145; G01M 11/335; G01M 11/33; G01M 11/3109; G01M 11/338
USPC ....................................................... 356/73.1
See application file for complete search history.

(56) References Cited

U.S. PATENT DOCUMENTS

| | | | | |
|---|---|---|---|---|
| 4,408,495 A * | 10/1983 | Couch | ............... | G01H 9/004 250/227.16 |
| 4,752,053 A * | 6/1988 | Boetzkes | ............... | B61L 23/00 346/167 R |
| 5,330,136 A * | 7/1994 | Colbaugh | ............... | B61L 1/06 246/122 R |
| 7,800,743 B1 * | 9/2010 | Huffman | ............... | H04B 10/85 356/73.1 |
| 7,872,736 B2 | 1/2011 | Rogers et al. | | |
| 7,940,389 B2 | 5/2011 | Rogers et al. | | |
| 8,264,676 B2 | 9/2012 | Kanellopoulos et al. | | |
| 8,520,197 B2 | 8/2013 | Handerek | | |
| 8,634,681 B2 | 1/2014 | Rogers | | |
| 8,708,664 B2 * | 4/2014 | Brookbank | ............... | F04B 47/06 310/87 |
| 8,760,639 B2 | 6/2014 | Handerek | | |
| 9,108,640 B2 | 8/2015 | Jackson | | |
| 2010/0166357 A1 * | 7/2010 | Huffman | ............... | G01M 5/00 385/12 |
| 2011/0199607 A1 | 8/2011 | Kanellopoulos et al. | | |
| 2011/0216996 A1 | 9/2011 | Rogers | | |
| 2011/0255077 A1 | 10/2011 | Rogers | | |

(Continued)

OTHER PUBLICATIONS

Fotech Solutions; Railways: Sound at the speed of light: Presentation; 4 pgs.

(Continued)

*Primary Examiner* — Tarifur Chowdhury
*Assistant Examiner* — Md M Rahman
(74) *Attorney, Agent, or Firm* — Christopher R. Carroll; The Small Patent Law Group, LLC

(57) ABSTRACT

Methods and systems for monitoring vibrations introduce baseline vibrations into a fiber optic cable with one or more of a designated frequency or a designated amplitude. Changes in the baseline vibrations are monitored using the fiber optic cable. Information about environmental conditions outside of the fiber optic cable and/or moving objects can be determined based at least in part on the changes in the baseline vibrations that are monitored. The information that is determined about the objects, such as vehicles, can be modified based on the changes in the baseline vibrations.

14 Claims, 4 Drawing Sheets

(56) References Cited

U.S. PATENT DOCUMENTS

| | | |
|---|---|---|
| 2012/0087619 A1 | 4/2012 | Rogers |
| 2012/0127459 A1 | 5/2012 | Handerek |
| 2012/0150370 A1* | 6/2012 | Oldknow ............ B61K 9/08 701/19 |
| 2013/0030725 A1* | 1/2013 | Friedlander ......... G01H 1/12 702/56 |
| 2013/0061688 A1 | 3/2013 | Hayward |
| 2013/0222811 A1 | 8/2013 | Handerek |
| 2013/0271769 A1 | 10/2013 | Handerek |
| 2013/0301037 A1 | 11/2013 | Handerek |

OTHER PUBLICATIONS

Fotech Solutions; Fibre Acoustic Monitoring for Railways; Nigel Leggett, COO Fotech Solutions Ltd—Nov. 2010; 24 pgs.

Fotech Solutions; Helios System; With additional functionality; 24 pgs.

* cited by examiner

VIBRATION MONITORING SYSTEM AND METHOD

FIELD

Embodiments of the subject matter disclosed herein relate to monitoring systems and methods

BACKGROUND

Some known systems sense vibrations propagating through the ground in order to detect the presence of one or more objects. These systems can examine the vibrations that are sensed in order to attempt to identify the objects, determine where the objects are located, and the like. One example of such systems senses ground vibrations using a fiber optic cable extending beneath or near rail tracks. While these fiber optic cables may have been placed along the rail track to provide network connectivity, some rail companies have the ability to use these fiber optic cables to monitor vibrations in the ground. These vibrations can be used to attempt to identify the passage of rail vehicles along the track.

One problem with these known systems is that the systems are not "vital" systems. For example, the systems may be unable to automatically correct changes in sensed vibrations that are caused by external factors. Changes in the weather and other factors may change the vibrations and/or the propagation of vibrations through the ground, and can hinder or block the ability of these systems to accurately identify rail vehicles based on the vibrations that are generated. These systems may suffer from incorrectly detecting a rail vehicle based on vibrations that are not caused by the rail vehicle, but that appear to be caused by a rail vehicle due to the impact of environmental conditions on the propagation of the vibrations. Similarly, these systems may suffer from failing to detect a rail vehicle based on vibrations that are caused by the rail vehicle, but that do not appear to be caused by a rail vehicle due to the impact of environmental conditions on the propagation of the vibrations.

BRIEF DESCRIPTION

In one embodiment of the invention, a method (e.g., for sensing vibrations) includes introducing baseline vibrations into a fiber optic cable with one or more of a designated frequency or a designated amplitude, monitoring changes in the baseline vibrations using the fiber optic cable, and determining information about environmental conditions outside of the fiber optic cable based at least in part on the changes in the baseline vibrations that are monitored.

In another embodiment, a system (e.g., a monitoring system) includes a control system and a sensing system. The control system is configured to introduce baseline vibrations into a fiber optic cable with one or more of a designated frequency or a designated amplitude. The sensing system is configured to monitor changes in the baseline vibrations using the fiber optic cable and to determine information about environmental conditions outside of the fiber optic cable based at least in part on the changes in the baseline vibrations that are monitored.

In another embodiment, a sensing system includes one or more sensors and one or more sensing processors. The one or more sensors are configured to examine light traveling through a fiber optic cable extending along and beneath a route traveled by vehicles. The one or more sensing processors are configured to monitor changes in baseline vibrations introduced into the fiber optic cable at designated times, and to determine information about environmental conditions outside of the fiber optic cable based at least in part on the changes in the baseline vibrations that are monitored.

BRIEF DESCRIPTION OF THE DRAWINGS

Reference is made to the accompanying drawings in which particular embodiments and further benefits of the invention are illustrated as described in more detail in the description below, in which.

DETAILED DESCRIPTION

One or more embodiments of a vibration monitoring system and method are described herein. These systems and methods can generate vibrations that propagate through a portion of the ground that includes one or more sensing cables. The sensing cable can be used to detect the vibrations. As one example, a fiber optic cable can be used as the sensing cable, with changes in refraction of light in the fiber optic cable being representative of the vibrations that propagate through, into, or around the cable. Based on the magnitude (e.g., amplitude), frequency, period, or the like, of the vibrations that are detected, the presence and/or location of one or more objects on the ground can be determined. For example, passage of a vehicle above the sensing cable can be detected, as well as the speed, direction of travel, size, or the like, of the vehicle. Optionally, changes in the vibrations can be used to identify damaged segments of a route being traveled upon by the vehicle.

In one aspect, the vibration monitoring systems and methods can detect vibrations caused by moving objects and determine information about the vibrations and/or objects based on the detected vibrations. This information that is determined can include peaks, waveforms, frequencies, amplitudes, or the like, in a frequency spectrum of the vibrations, or other information. This information can be used to identify the moving object, determine a location of the moving object, determine a speed of the object, identify a portion of a route being traveled on by the object that may be damaged, or the like.

The vibrations may change due to factors other than the moving objects (e.g., moving vehicles, damaged routes, or the like). For example, in different environmental conditions (e.g., different times, seasons, periods of condensation, etc.), the same object may cause the vibration monitoring systems and methods to detect different vibrations. The differences between the detected vibrations can be caused by the changing environmental conditions instead of the object of interest. The systems and methods can identify these differences caused by the environmental conditions and modify the information that is determined based on the detected vibrations to account for the changes caused by the environmental conditions. The systems and methods can therefore self-correct changes in the vibrations that are not caused by the objects of interest in order to improve the vitality, accuracy, precision, and functionality of the systems and methods.

Figure 1:
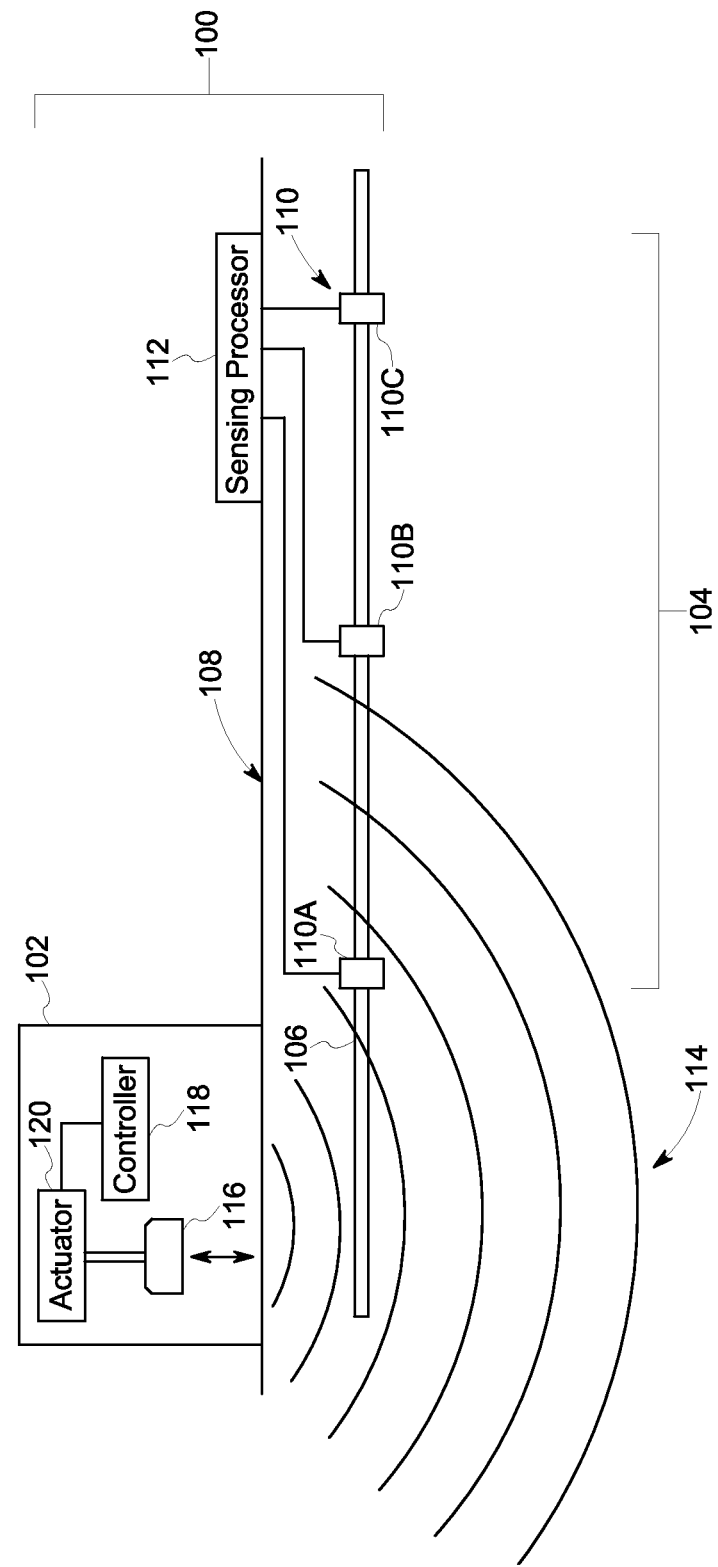
FIG. 1 is a schematic diagram of a vibration monitoring system according to one embodiment.

FIG. 1 is a schematic diagram of a vibration monitoring system 100 according to one embodiment. The system 100 includes a control system 102 that generates baseline vibrations that are used to detect changing environmental conditions. The system 100 also includes a sensing system 104 that detects vibrations caused by objects of interest (e.g., vibrations of interest) and the baseline vibrations. Optionally, the system 100 may include multiple sensing systems 104 that separately detect the vibrations of interest or the baseline vibrations.

A sensing device 106 is disposed beneath a surface 108 of the ground (e.g., the surface of the earth or another surface). In one embodiment, the sensing device 106 is a fiber optic cable that communicates information between two or more locations by internally refracting light within the device 106. Alternatively, the sensing device 106 may be another type of cable that can be used to detect vibrations in the ground. The sensing system 104 includes several sensors 110 (e.g., sensors 110A-C) operably connected with the sensing device 106 at different locations. For example, the sensors 110 may be light-sensitive devices that measure changes in how light is internally reflected or otherwise refracted in the sensing device 106. The number and arrangement of the sensors 110 is provided merely as one example. As described herein, the sensing device 106 can be used to sense vibrations propagating through the ground. Alternatively, another device, system, or apparatus may be used as the sensing device 106 to detect the vibrations. For example, one or more accelerometers, seismometers, or the like, may sense the vibrations.

A sensing processor 112 represents one or more computer processors (e.g., microprocessors), hardware circuits or circuitry, or a combination thereof, that examine data that is output by the sensors 110 to measure the vibrations propagating through the sensing device 106. For example, the sensors 110 may be conductively coupled with the sensing processor 112 by one or more wires, cables, or the like, and/or may be wirelessly connected with the sensing processor 112 such that the sensors 110 can communicate data representative of the vibrations detected using the sensing device 106 to the sensing processor 112.

The sensing processor 112 examines the data received from the sensors 110 to identify the vibrations propagating through, into, and/or around the sensing device 106. Based on these vibrations and/or changes in the vibrations, the sensing processor 112 can determine information about an object on the surface 108. This information can include an identification of the object of interest on the surface 108, a location of a moving object of interest on the surface 108, a moving speed of the object of interest, a size of the object of interest, or the like. For example, different objects, different locations of the objects, different speeds of the objects, and/or different sizes of the objects may be associated with different patterns or waveforms of the vibrations that are determined by the sensing processor 112 and detected using the sensing device 106.

In order to account for changes in environmental conditions and the impact of these changes in the vibrations caused by objects of interest, the control system 102 can generate baseline vibrations into the ground where the sensing device 106 is located. These baseline vibrations may be generated at pre-designated times and/or during pre-designated time periods. The baseline vibrations may be generated with pre-designated amplitudes and/or frequencies. As described below, these baseline vibrations may be detected by the sensing system 104 and used to modify and correct changes to vibrations of interest that are caused by environmental conditions.

Figure 2:
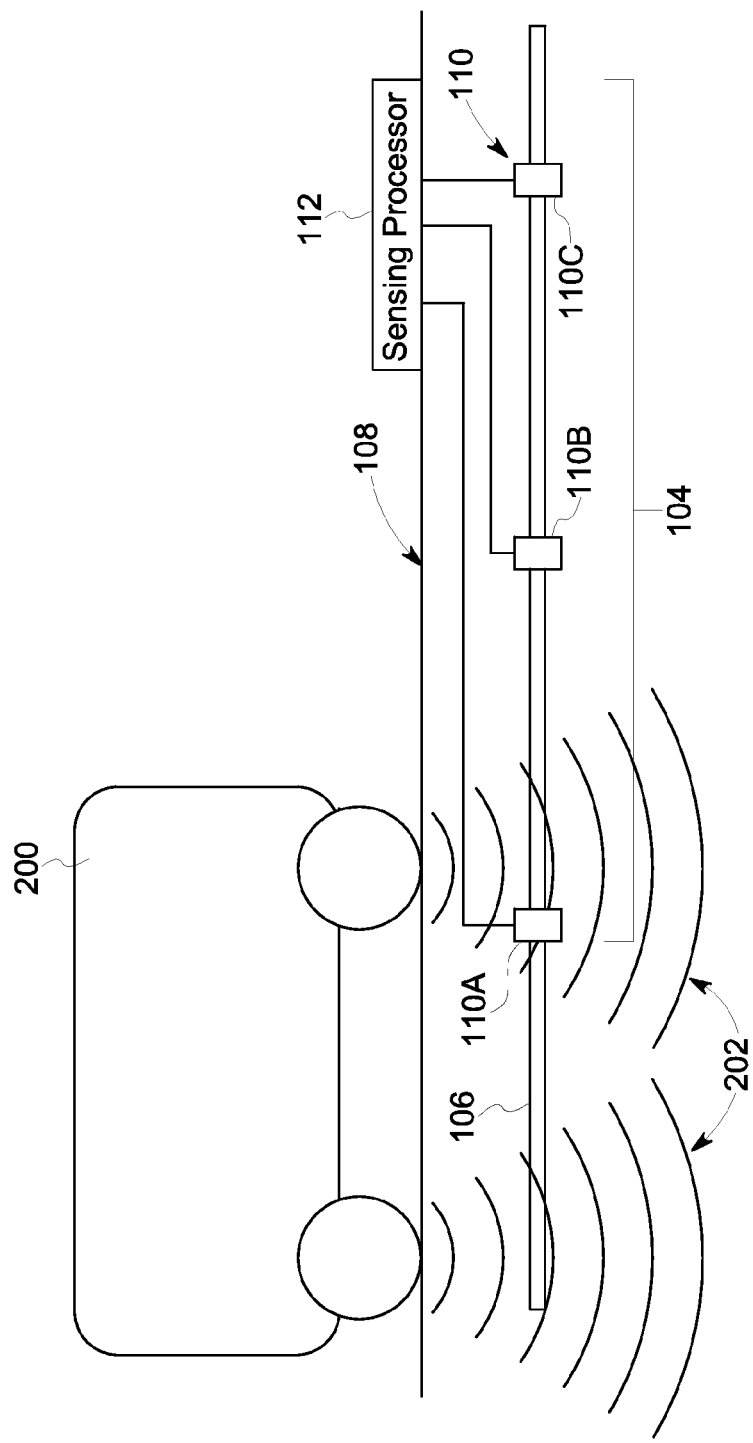
FIG. 2 schematically illustrates a sensing system of the vibration monitoring system shown in FIG. 1 during movement of an object of interest according to one embodiment.

FIG. 2 schematically illustrates the sensing system 104 of the vibration monitoring system 100 shown in FIG. 1 during movement of an object of interest 200 according to one embodiment. The object of interest 200 is shown as a vehicle, such as a rail vehicle, automobile, mining vehicle, or the like, but alternatively may be another object. For example, the sensing device 106 can extend along a route, such as a railway track, for sensing vibrations generated by a vehicle, such as a rail vehicle, traveling along the route. During movement of the object of interest 200 on or near the surface 108, vibrations of interest 202 are generated in the ground beneath the surface 108. The vibrations of interest are vibrations that differ from baseline vibrations, as described herein. These vibrations of interest 202 propagate through the ground to the sensing device 106. The vibrations of interest 202 can change the manner in which light is reflected within the sensing device 106. These changes are detected by the sensors 110 as changes in intensities of light, changes in intensities of light at different wavelengths, or the like. The sensors 110 output data representative of the light and/or changes in the manner in which the light is reflected within the sensing device 106. This data is communicated to the sensing processor 112.

Figure 3:
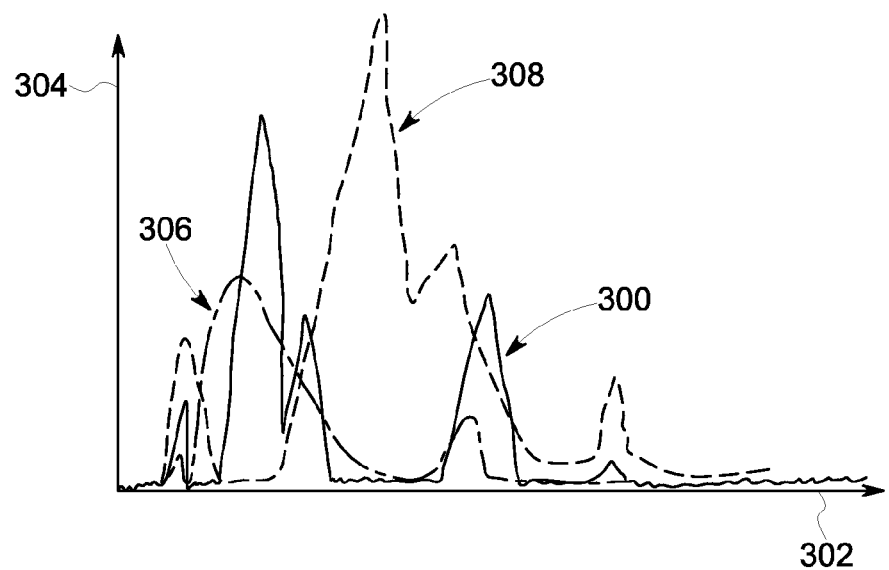
FIG. 3 illustrates one example of a frequency spectrum of vibrations of interest generated by movement of the object of interest shown in FIG. 2 as detected by the sensing system shown in FIG. 1.

FIG. 3 illustrates one example of a frequency spectrum of vibrations of interest 300 generated by movement of the object of interest 200 shown in FIG. 2 as detected by the sensing system 104. The vibrations of interest 300 are shown alongside a horizontal axis 302 representative of frequencies of the vibrations of interest 300 and a vertical axis 304 representative of amplitude or magnitude of the vibrations of interest 300 at the different frequencies.

The vibrations of interest 300 can represent the vibrations detected by the sensing system 104 during movement of the object of interest 200. These vibrations of interest 300 can represent a signature or waveform that is associated with the object of interest 200. When the vibrations of interest 300 are detected, the object of interest 200 can be identified by the sensing processor 112 by comparing the vibrations of interest 300 to different signatures or waveforms that are associated with different objects of interest 200, and identifying the object of interest 200 based on this comparison. For example, the signatures or waveforms may be defined as designated peaks in the vibrations of interest 300 that are located at designated frequencies and/or within a designated range of frequencies. If the vibrations of interest 300 have peaks in the designated frequencies and/or designated range of frequencies, then the vibrations of interest 300 may be identified as the object of interest 200 that is associated with the designated frequencies and/or designated range of frequencies of the signature or waveform. Optionally, different objects of interest 200 may be associated with different signatures or waveforms, different speeds of different objects of interest 200 may be associated with different signatures or waveforms, different locations of objects of interest 200 may be associated with different signatures or waveforms, and the like, so that the sensing system 104 may be able to identify different objects of interest 200, different speeds of objects of interest 200, different locations of the objects of interest 200, and the like.

The sensing processor 112 may not be able to identify the object of interest 200 due to changes in environmental conditions, however. For example, the density, makeup, mass, or the like, of the ground may change at different times of the day, during different seasons, and during different weather conditions (e.g., rain, snow, ice, dry weather, etc.). These different environmental conditions can impact the manner in which the vibrations of interest 202 (shown in FIG. 2) propagate through the ground and are detected by the sensing system 104.

For example, during first environmental conditions (e.g., dry weather during daylight of a summer month), the vibrations of interest may appear as the vibrations of interest 300 shown in FIG. 3. But, during different, second environmental conditions (e.g., wet weather during the night of a spring month), the same object of interest 200 may generate the vibrations of interest that are detected by the sensing system 104 as vibrations of interest 306 in FIG. 3. During different, third environmental conditions (e.g., ice on the ground during the winter), the same object of interest 200 may generate the vibrations of interest that are detected by the sensing system 104 as vibrations of interest 308 in FIG. 3. The changing environmental conditions can prevent the sensing system 104 from being able to accurately identify the object of interest 200 based on the vibrations that are detected.

Returning to the description of the vibration monitoring system 100 shown in FIG. 1, the system 100 can adapt to changes in the environmental conditions by repeatedly monitoring changes in baseline vibrations generated by the system 100 and using these changes to modify (e.g., correct) the information that is determined from the vibrations of interest generated by the objects 200 (shown in FIG. 2). The control system 102 may generate baseline vibrations 114 in the ground by moving a weighted object 116 relative to the ground. The weighted object 116 can be a weight, a body with a moveable eccentric mass, or another type of body that can generate vibrations in the ground when moved relative to the ground. The weighted object 116 shown in FIG. 1 can be moved toward the surface 108 of the ground to strike the ground and generate the baseline vibrations 114. The weighted object 116 can then be moved away from the ground for preparation in striking the ground again to generate additional baseline vibrations 114.

The control system 102 includes a controller 118 that represents one or more computer processors (e.g., microprocessors), hardware circuits or circuitry, or a combination thereof. The controller 118 controls generation of the baseline vibrations 114 by controlling movement of the object 116. An actuator 120 moves the object 116 pursuant to instruction signals received from the controller 116. The actuator 120 can include a motor, electromagnet, pneumatically controlled piston, or another device capable of moving the object 116 to generate the baseline vibrations 114. The controller 118 generates the instruction signals and communicates the signals to the actuator 120 via one or more wired and/or wireless connections. The signals can indicate the times at which the actuator 120 is to move the object 116 to generate the baseline vibrations 114, how long of a time period that the actuator 120 is to generate the baseline vibrations 114, and/or how to move the object 116 to generate the baseline vibrations 114. With respect to instructions on how to move the object 116, these instructions can tell the actuator 120 how high to lift the object 116 off the surface 108 before dropping or moving the object 116 toward the surface 108, how quickly to move the object 116 toward the surface 108 (or whether to drop the object 116 onto the surface 108), how many times to move the object 116, and/or how frequently the object 116 should be moved. If the object 116 is to be dropped onto or otherwise moved into contact with the surface 108 or another object in contact with the surface 108 to generate the baseline vibrations 114, then the instructions can dictate how fast the object 116 is moved toward the surface 108 or other object, how far the object 116 is away from the surface 108 when the object 116 is dropped or moved toward the surface 108, and the like. If the object 116 is moved relative to the surface 108 without striking the surface 108 or an object on the surface 108 (e.g., the object 116 is an eccentric mass that is rotated or otherwise moved relative to the surface 108 to generate the baseline vibrations 114), then the instructions can dictate how rapidly the object 116 is moved, how long the object 116 is moved, or the like.

Figure 4:
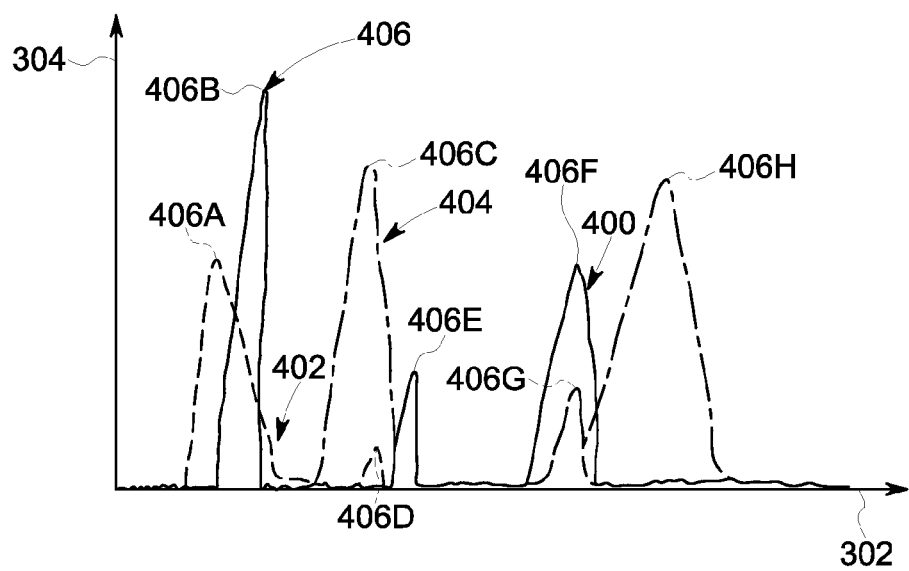
FIG. 4 illustrates a frequency spectrum of baseline vibrations generated by a control system shown in FIG. 1 during different environmental conditions according to one embodiment.

FIG. 4 illustrates a frequency spectrum of baseline vibrations 400, 402, 404 generated by the control system 102 shown in FIG. 1 during different environmental conditions according to one embodiment. The baseline vibrations 400, 402, 404 are shown alongside the horizontal and vertical axes 302, 304 described above in connection with FIG. 3. The baseline vibrations 400, 402, 404 are generated by the control system 102 by moving the same object 116 (shown in FIG. 1) in the same manner, but at different times and under different environmental conditions. For example, the baseline vibrations 400 may be sensed by the sensing system 104 responsive to a ten pound (or 4.5 kilogram) object 116 being dropped onto the surface 108 (shown in FIG. 1) from one foot (or thirty centimeters) above the surface 108 during dry conditions during the daytime. The baseline vibrations 402, 404 may be generated and sensed during other conditions. For example, the baseline vibrations 402 may be generated by dropping the same ten pound (or 4.5 kilogram) object 116 being onto the surface 108 from one foot (or thirty centimeters) above the surface 108 during rain, when there is snow on the surface 108, during nighttime, or the like. The baseline vibrations 404 may be generated by dropping the same ten pound (or 4.5 kilogram) object 116 being onto the surface 108 from one foot (or thirty centimeters) above the surface 108 when there is ice on the surface 108.

The control system 102 can generate the baseline vibrations at designated times, such as times that are known to the sensing system 104. The control system 102 can generate the baseline vibrations at times that are known or communicated to the sensing system 104 (e.g., by the controller 118 of the control system 102 or another device) so that the sensing system 104 can differentiate between baseline vibrations and vibrations of interest.

In one aspect, the sensing processor 112 can determine that the system 100 is malfunctioning based at least in part on the baseline vibrations. For example, the sensing processor 112 may be aware of the times at which the baseline vibrations are generated by the control system 102. If the sensing processor 112 does not detect the baseline vibrations at times that correspond to when the baseline vibrations are generated, then the sensing processor 112 can determine that the system 100 is malfunctioning. Responsive to determining this, the sensing processor 112 can communicate one or more warning signals to another location, such as a repair facility, dispatch facility, or the like, to warn of the malfunction of the system 100, and/or to request inspection, repair, maintenance, or the like, of the system 100.

The baseline vibrations 400 can be designated as a calibration signature. The sensing system 104 may periodically, regularly, randomly, or otherwise repeatedly re-determine the baseline vibrations that are used as the calibration signature. Subsequently obtained baseline vibrations 402, 404 can be compared to the calibration signature in order to determine how the vibrations sensed by the sensing system 104 change due to the changing environmental conditions. For example, the sensing system 104 can sense the baseline vibrations 402 and compare the baseline vibrations 402 to the baseline vibrations 400 by comparing characteristics of the vibrations 400, 402 with each other. These characteristics can include, but are not limited to, locations (e.g., frequencies) of peaks 406 (e.g., peaks 406A-H), widths of the peaks 406 (e.g., the ranges of frequencies over which one or more peaks 406 extend, heights of peaks 406 (e.g., the amplitude of one or more of the peaks 406 along the vertical axis 304), and the like.

In the illustrated example, the sensing system 104 can compare the baseline vibrations 400, 402 and determine that the peak 406B in the baseline vibration 400 has moved to a lower frequency and/or has a reduced amplitude as the peak 406A in the baseline vibration 402, that the peak 406E in the baseline vibration 400 has moved to a lower frequency and/or has a reduced amplitude as the peak 406D in the baseline vibration 402, and/or that the peak 406F in the baseline vibration 400 has the same or similar frequency as the peak 406G (e.g., is within a designated range of the peak 406F, such as 1%, 5%, 10%, or the like) and/or has a reduced amplitude as the peak 406G in the baseline vibration 402.

The sensing system 104 can use these differences between the baseline vibrations 400, 402 to correct the information about the objects 200 that is determined from the vibrations of interest 300, 306, 308 shown in FIG. 3. For example, due to changing environmental conditions, the baseline vibrations 400, 402 appear to shift to lower frequencies and/or have reduced amplitudes, as described above. To correct for the impact of the changing environmental conditions on the vibrations of interest, the sensing system 104 can measure frequencies and/or amplitudes from the vibrations of interest, and then modify these frequencies and/or amplitudes. For example, the sensing system 104 can increase the value of the measured frequencies at which peaks appear in the vibrations of interest 300, 306, 308, can increase the value of the amplitudes of the peaks in the vibrations of interest 300, 306, 308, or the like. The frequencies and/or amplitudes of the peaks in the vibrations of interest 300, 306, 308 can be increased by the same amount that the frequencies and/or amplitudes of the peaks in the baseline vibrations 400, 402 decreased, or may be increased by an amount that is at least partially based on the decrease in the peaks in the baseline vibrations 400, 402. While the sensing system 104 may not be actually changing the frequencies, amplitudes, or the like, of the peaks, the sensing system 104 can change the measured frequencies, amplitudes, or the like, that are measured from the vibrations of interest and used to identify information about the object 200.

As another example, the sensing system 104 can compare the baseline vibrations 400, 404 and determine that the peak 406B in the baseline vibration 400 has moved to a higher frequency and/or has a reduced amplitude as the peak 406C in the baseline vibration 404, and/or that the peak 406F in the baseline vibration 400 has moved to a higher frequency and/or has an increased amplitude as the peak 406H in the baseline vibration 404. The sensing system 104 can use these differences between the baseline vibrations 400, 404 to correct information determined from the vibrations of interest 300, 306, 308 shown in FIG. 3. For example, due to changing environmental conditions, the baseline vibrations 400, 402 appear to shift to higher frequencies and/or have increased amplitudes, as described above. To correct for the impact of the changing environmental conditions on the vibrations of interest, the sensing system 104 can modify the frequencies and/or amplitudes that are measured from the vibrations of interest. For example, the sensing system 104 can decrease the frequencies at which peaks appear in the vibrations of interest 300, 306, 308, can decrease the amplitudes of the peaks in the vibrations of interest 300, 306, 308, or the like. The frequencies and/or amplitudes of the peaks in the vibrations of interest 300, 306, 308 can be decreased by the same amount that the frequencies and/or amplitudes of the peaks in the baseline vibrations 400, 404 increased, or may be decreased by an amount that is at least partially based on the increase in the peaks in the baseline vibrations 400, 404.

In one embodiment, the sensing system 104 can determine information about the environmental conditions based on the differences between the baseline vibrations. For example, based on decreases in frequency for one or more peaks in the baseline vibrations, the sensing system 104 can determine that the ground is becoming softer, such as due to rainfall. Alternatively, based on increases in frequency for one or more peaks in the baseline vibrations, the sensing system 104 can determine that the ground is becoming harder, such as due to ice forming on and/or in the ground. The sensing system 104 can use this information about the environmental conditions to change vibrations of interest, as described above. Additionally or alternatively, the sensing system 104 can use the information about the environmental conditions to warn operators of vehicles of dangerous conditions. For example, the sensing system 104 can generate signals that are communicated to vehicles to warn the vehicles of potential ice, rain, or the like, that the sensing system 104 may have detected.

Once the information determined from the vibrations of interest is corrected, the vibrations of interest can be referred to as corrected or modified vibrations of interest. For example, a waveform, measured frequency of a peak, measured amplitude of a peak, or the like, in the vibration of interest may be corrected by changing the measured waveform, measured frequency, and/or measured amplitude to a modified waveform, frequency and/or amplitude. This corrected or modified information can be compared to the signatures or waveforms associated with different objects of interest. Depending on which signatures or waveforms more closely match or otherwise correspond to the corrected or modified information, the sensing system 104 may be able to identify the object of interest, the speed of the object of interest, the location of the object of interest, the size of the object of interest, or the like, based at least in part on the corrected or modified information. The identified object, speed, location, size, or the like can be used for a variety of purposes, such as to activate a warning system or signal that a vehicle is approaching, to determine if a vehicle is traveling too fast or too slow, to generate control signals that automatically slow down or speed up the vehicle based on the speed that is determined, or the like. For example, based on the corrected information, the sensing system 104 can determine a size of a moving vehicle, the location of the vehicle, and/or how fast the vehicle is moving. The size of the vehicle may be used by the sensing system 104 to differentiate between different vehicles and thereby identify the vehicle. Based on the location of the vehicle and the speed of the vehicle, the sensing system 104 can generate control signals that are communicated to one or more locations, such as a dispatch center, where the identify, location, and/or speed of the vehicle can be displayed to one or more operators to monitor movements of the vehicle. Optionally, these control signals may be communicated to a signal (e.g., a light or a gate) to actuate the signal and warn other vehicles of the movement of the detected vehicle.

Figure 5:
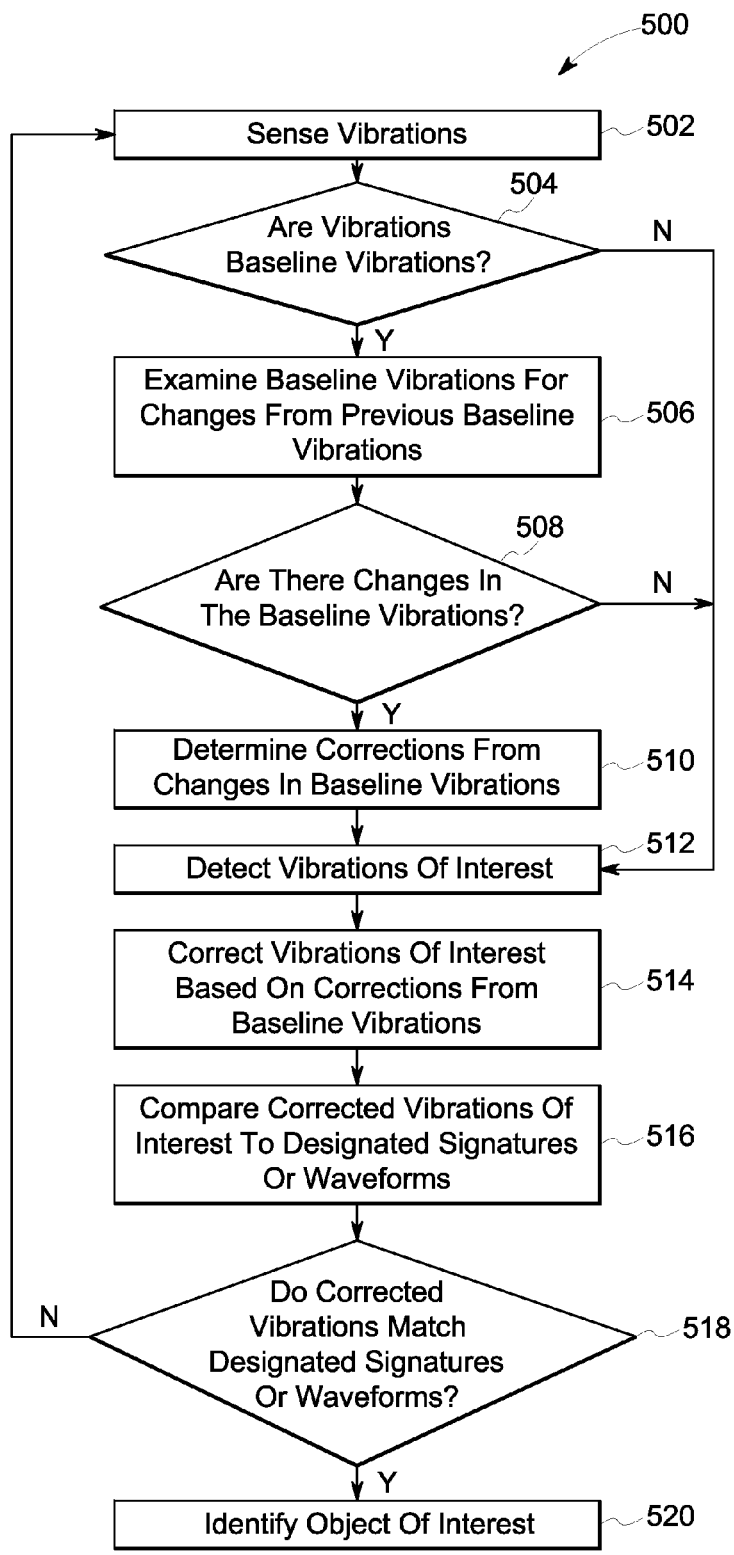
FIG. 5 illustrates a flowchart of a method for monitoring vibrations according to one embodiment.

FIG. 5 illustrates a flowchart of a method 500 for monitoring vibrations according to one embodiment. The method 500 can be performed by the monitoring system 100 shown in FIG. 1 and described above. At 502, vibrations are sensed. For example, vibrations propagating through the ground may be detected. The vibrations can be sensed by examining changes in light being conveyed through a cable, such as a fiber optic cable. Alternatively, the vibrations may be sensed in another manner, such as by using one or more accelerometers or other devices. At 504, a determination is made as to whether the sensed vibrations are baseline vibrations. The baseline vibrations may be generated at known or designated times, or within known or designated time periods. If the vibrations are sensed at the known or designated times, within a designated time period following the known or designated times (e.g., within thirty seconds or another time period), within the known or designated time periods, or the like, then the sensed vibrations may be identified as baseline vibrations. As a result, flow of the method 500 can proceed to 506. On the other hand, if the sensed vibrations are not sensed at times that would correspond with the generation of the baseline vibrations, then flow of the method 500 can proceed to 512, which is described below.

At 506, the baseline vibrations are examined for changes from one or more previous baseline vibrations. For example, the baseline vibrations sensed at 502 can be compared with previously sensed baseline vibrations to determine if shapes, waveforms, peaks, or the like, in the previously sensed baseline vibrations have moved (e.g., changed which frequencies the peaks appear at), changed shape (e.g., have larger or smaller amplitudes, are wider or narrower, etc.), or otherwise changed.

At 508, a determination is made as to whether the baseline vibrations have changed. If the baseline vibrations have changed from one or more previously sensed baseline vibrations, then environmental conditions may be altering the propagation of vibrations through the ground. As a result, the vibrations generated by objects of interest also may be altered by the environmental conditions in a similar manner. If the baseline vibrations have changed or have changed by at least a significant amount (e.g., the frequency of a peak changes by at least a designated, non-zero amount, such as 1%, 5%, 10%, or another amount), then flow of the method 500 can proceed to 510. On the other hand, if the baseline vibrations have not changed, or have not changed by a significant amount, then flow of the method 500 can proceed to 512, which is described below.

At 510, corrections to sensed vibrations are determined from the changes in the baseline vibrations. For example, the change in the frequencies at which one or more peaks appear in the baseline vibrations, the change in amplitudes of the peaks, or other changes, may be calculated. At 512, vibrations of interest are sensed. If the vibrations sensed at 504 are not baseline vibrations, then the sensing of vibrations at 504 and 512 may be the same operation of sensing the same vibrations. Because the vibrations are not baseline vibrations used to determine corrections to account for changing environmental conditions, the vibrations may be vibrations of interest. These vibrations may be used to identify an object of interest, speed of the object of interest, a location of the object of interest, or the like.

At 514, the vibrations of interest are corrected based on the corrections determined from the baseline vibrations. For example, one or more frequencies, amplitudes, waveforms, or the like, that are determined from the vibrations of interest can be modified based on the corrections determined from the baseline vibrations. If no corrections were determined based on changes in the baseline vibrations (e.g., the baseline vibrations were not affected by the environmental conditions or were not significantly affected such that one or more peaks did not shift frequencies and/or change amplitudes by at least a designated, non-zero amount), then the information obtained from the vibrations of interest may not be modified. On the other hand, if corrections were determined based on changes in the baseline vibrations, then these corrections may be applied to the information determined from the vibrations of interest to form corrected or modified information from the vibrations of interest.

At 516, the corrected vibrations of interest (or vibrations of interest that were not corrected due to the lack of significant changes to the baseline vibrations) are compared to one or more designated signatures or waveforms. As described above, different signatures or waveforms may include different patterns, arrangements, or the like, of peaks, and may be representative of different types of objects of interest, different moving speeds of different objects of interest, different locations of objects of interest, etc.

At 518, a determination is made as to whether the corrected vibrations of interest (or vibrations of interest that were not corrected due to the lack of significant changes to the baseline vibrations) match one or more of the signatures or waveforms. For example, a determination may be made as to whether the peaks or other shapes of the frequency spectrum of the corrected vibrations of interest more closely match the peaks or other shapes of a signature or waveform than one or more other signatures or waveforms. If so, then flow of the method 500 can proceed to 520. For example, the corrected vibrations of interest may closely match the peaks of a signature or waveform representative of a particular object of interest, a particular speed of an object of interest, a particular location of an object of interest, or the like. On the other hand, if the corrected vibrations of interest do not match one or more of the signatures or waveforms, then the vibrations of interest may not represent an object of interest, a speed of an object of interest, a location of an object of interest, or the like. As a result, flow of the method 500 can return to 502 for additional vibrations to be sensed.

At 520, information about an object of interest is determined based at least in part on the vibrations of interest. For example, the object of interest, the location of the object of interest, the speed of the object of interest, or the like, that is associated with a signature or waveform that more closely matches the corrected vibrations of interest than other signatures or waveforms may be identified. After this identification, flow of the method 500 can return to 502 so that additional vibrations can be sensed, corrected, and/or used to identify information about an object of interest.

In one embodiment, a method (e.g., for sensing vibrations) includes introducing baseline vibrations into a fiber optic cable with one or more of a designated frequency or a designated amplitude, monitoring changes in the baseline vibrations using the fiber optic cable, and determining information about environmental conditions outside of the fiber optic cable based at least in part on the changes in the baseline vibrations that are monitored.

In one aspect, the method also can include monitoring second vibrations generated by movement of an object using the fiber optic cable, determining information about the second vibrations, and modifying the information about the second vibrations based at least in part on the changes in the baseline vibrations that are monitored.

In one aspect, modifying the information about the second vibrations can include one or more of shifting a frequency of one or more peaks in a frequency spectrum of the second vibrations or changing an amplitude of the one or more peaks in the frequency spectrum of the second vibrations.

In one aspect, modifying the information about the second vibrations can include one or more of shifting the frequency of one or more peaks in the frequency spectrum of the second vibrations or changing the amplitude of the one or more peaks in the frequency spectrum of the second vibrations by an amount that matches the changes in the baseline vibrations.

In one aspect, monitoring the changes in the baseline vibrations can include identifying one or more of a changing frequency of one or more peaks in a frequency spectrum of the baseline vibrations or a changing amplitude of the one or more peaks in the frequency spectrum of the baseline vibrations.

In one aspect, the method also can include monitoring second vibrations generated by movement of an object using the fiber optic cable, and distinguishing between the second vibrations and the baseline vibrations based at least in part on times at which the baseline vibrations are generated.

In one aspect, introducing the baseline vibrations includes a control system automatically moving a weighted object portion of the control system relative to a surface above the fiber optic cable.

In one aspect, introducing the baseline vibrations into the fiber optic cable with a control system automatically imparting a force onto a surface of ground in which the fiber optic cable is buried. The method also can include receiving (at one or more processors) first information about monitored second vibrations of the fiber optic cable generated by movement of a vehicle upon the surface, modifying (with the one or more processors) the first information of the monitored second vibrations based at least in part on the changes in the baseline vibrations that are monitored, and identifying (with the one or more processors) second information about the vehicle based at least in part on the first information that is modified.

In another embodiment, a system (e.g., a monitoring system) includes a control system and a sensing system. The control system is configured to introduce baseline vibrations into a fiber optic cable with one or more of a designated frequency or a designated amplitude. The sensing system is configured to monitor changes in the baseline vibrations using the fiber optic cable and to determine information about environmental conditions outside of the fiber optic cable based at least in part on the changes in the baseline vibrations that are monitored.

In one aspect, the sensing system also can be configured to monitor second vibrations generated by movement of an object using the fiber optic cable, determine information about the second vibrations, and modify the information about the second vibrations based at least in part on the changes in the baseline vibrations that are monitored.

In one aspect, the sensing system can be configured to modify the information about the second vibrations by one or more of shifting a frequency of one or more peaks in a frequency spectrum of the second vibrations or changing an amplitude of the one or more peaks in the frequency spectrum of the second vibrations.

In one aspect, the sensing system can be configured to modify the information about the second vibrations by one or more of shifting the frequency of one or more peaks in the frequency spectrum of the second vibrations or changing the amplitude of the one or more peaks in the frequency spectrum of the second vibrations by an amount that matches the changes in the baseline vibrations.

In one aspect, the sensing system can be configured to monitor the changes in the baseline vibrations by identifying one or more of a changing frequency of one or more peaks in a frequency spectrum of the baseline vibrations or a changing amplitude of the one or more peaks in the frequency spectrum of the baseline vibrations.

In one aspect, the sensing system can be configured to monitor second vibrations generated by movement of an object using the fiber optic cable and to distinguish between the second vibrations and the baseline vibrations based at least in part on times at which the baseline vibrations are generated.

In one aspect, the control system can be configured to introduce the baseline vibrations by automatically moving a weighted object portion of the control system relative to a surface above the fiber optic cable.

In one aspect, the control system can be configured to introduce the baseline vibrations into the fiber optic cable by system automatically imparting a force onto a surface of ground in which the fiber optic cable is buried. The sensing system also can be configured to determine first information about monitored second vibrations of the fiber optic cable generated by movement of a vehicle upon the surface, to modify the first information of the monitored second vibrations based at least in part on the changes in the baseline vibrations that are monitored, and to identify second information about the vehicle based at least in part on the first information that is modified.

In one aspect, the sensing system can be configured to receive information about monitored second vibrations from one or more sensors operably connected with the fiber optic cable, where the second vibrations are created by movement of a vehicle along a route. The sensing system also can be configured to modify the information about the monitored second vibrations based at least in part on the changes in the baseline vibrations and to identify information about the vehicle based at least in part on the information about the monitored second vibrations that is modified.

In another embodiment, a sensing system includes one or more sensors and one or more sensing processors. The one or more sensors are configured to examine light traveling through a fiber optic cable extending along and beneath a route traveled by vehicles. The one or more sensing processors are configured to monitor changes in baseline vibrations introduced into the fiber optic cable at designated times, and to determine information about environmental conditions outside of the fiber optic cable based at least in part on the changes in the baseline vibrations that are monitored.

In one aspect, the one or more sensing processors also can be configured to monitor vibrations of interest generated by movement of an object of interest using the fiber optic cable, modify the vibrations of interest based at least in part on the changes in the baseline vibrations that are monitored, and identify information about the object of interest based at least in part on the vibrations of interest that are modified.

In one aspect, the one or more sensing processors can be configured to modify the vibrations of interest by one or more of shifting a frequency of one or more peaks in a frequency spectrum of the vibrations of interest or changing an amplitude of the one or more peaks in the frequency spectrum of the vibrations of interest.

In one aspect, the one or more sensing processors can be configured to modify the vibrations of interest by one or more of shifting the frequency of one or more peaks in the frequency spectrum of the vibrations of interest or changing the amplitude of the one or more peaks in the frequency spectrum of the vibrations of interest by an amount that matches the changes in the baseline vibrations.

Components of the systems described herein may include or represent hardware circuits or circuitry that include and/or are connected with one or more processors, such as one or more computer microprocessors. The operations of the methods described herein and the systems can be sufficiently complex such that the operations cannot be mentally performed by an average human being or a person of ordinary skill in the art within a commercially reasonable time period. For example, the examination of the vibrations may take into account a large amount of information, may rely on relatively complex computations, and the like, such that such a person cannot complete the examination of the vibrations within a commercially reasonable time period to correct vibrations measured during passage of a vehicle. The hardware circuits and/or processors of the systems described herein may be used to significantly reduce the time needed to obtain and examine the vibrations.

As used herein, a structure, limitation, or element that is "configured to" perform a task or operation is particularly structurally formed, constructed, programmed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, programming of the structure or element to perform the corresponding task or operation in a manner that is different from an "off-the-shelf" structure or element that is not programmed to perform the task or operation, and/or denotes structural requirements of any structure, limitation, or element that is described as being "configured to" perform the task or operation.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended clauses, along with the full scope of equivalents to which such clauses are entitled. In the appended clauses, the terms "including" and "in which" are used as the plain-English equivalents of the respective terms "comprising" and "wherein." Moreover, in the following clauses, the terms "first," "second," and "third," etc. are used merely as labels, and are not intended to impose numerical requirements on their objects. Further, the limitations of the following clauses are not written in means-plus-function format and are not intended to be interpreted based on 35 U.S.C. §112(f), unless and until such clause limitations expressly use the phrase "means for" followed by a statement of function void of further structure.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter may include other examples that occur to those of ordinary skill in the art. Such other examples are intended to be within the scope of the clauses if they have structural elements that do not differ from the literal language of the clauses, or if they include equivalent structural elements with insubstantial differences from the literal languages of the clauses.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "an embodiment" or "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described systems and methods without departing from the spirit and scope of the inventive subject matter herein involved, it is intended that all of the subject matter of the above description or shown in the accompanying drawings shall be interpreted merely as examples illustrating the inventive concept herein and shall not be construed as limiting the inventive subject matter.

The invention claimed is:

1. A method comprising:
introducing baseline vibrations into a fiber optic cable, the baseline vibrations generated with one or more of a designated frequency or a designated amplitude by automatically imparting a force onto a surface of ground in which the fiber optic cable is buried;
monitoring changes in the baseline vibrations using the fiber optic cable;
determining information about environmental conditions outside of the fiber optic cable based at least in part on the changes in the baseline vibrations that are monitored;
monitoring second vibrations generated by movement of a vehicle using the fiber optic cable;
determining information about the second vibrations;
modifying the information about the second vibrations by one or more of shifting a frequency of one or more peaks in a frequency spectrum of the second vibrations or changing an amplitude of the one or more peaks in the frequency spectrum of the second vibrations by an amount that matches the changes in the baseline vibrations; and
determining information about the vehicle based at least in part on the information about the second vibrations that is modified.

2. The method of claim 1, wherein monitoring the changes in the baseline vibrations includes identifying one or more of a changing frequency of one or more peaks in a frequency spectrum of the baseline vibrations or a changing amplitude of the one or more peaks in the frequency spectrum of the baseline vibrations.

3. The method of claim 1, further comprising distinguishing between the second vibrations and the baseline vibrations based at least in part on times at which the baseline vibrations are generated.

4. The method of claim 1, wherein introducing the baseline vibrations includes a control system automatically moving a weighted object portion of the control system relative to the surface above the fiber optic cable.

5. The method of claim 1, further comprising:
receiving, at one or more processors, first information about the second vibrations that are monitored by the fiber optic cable and generated by movement of a vehicle upon the surface;
modifying, with the one or more processors, the first information of the second vibrations that are monitored based at least in part on the changes in the baseline vibrations that are monitored; and
identifying, with the one or more processors, second information about the vehicle based at least in part on the first information that is modified.

6. A system comprising:
a control system configured to introduce baseline vibrations into a fiber optic cable, the baseline vibrations generated with one or more of a designated frequency or a designated amplitude, the control system also configured to introduce the baseline vibrations into the fiber optic cable by automatically imparting a force onto a surface of ground in which the fiber optic cable is buried; and
a sensing system configured to monitor changes in the baseline vibrations using the fiber optic cable and to determine information about environmental conditions outside of the fiber optic cable based at least in part on the changes in the baseline vibrations that are monitored,
wherein the sensing system is configured to monitor second vibrations generated by movement of a vehicle using the fiber optic cable, to determine information about the second vibrations, and to modify the information about the second vibrations by one or more of shifting a frequency of one or more peaks in a frequency spectrum of the second vibrations or changing an amplitude of the one or more peaks in the frequency spectrum of the second vibrations by an amount that matches the changes in the baseline vibrations, and
the sensing system is configured to identify information about the vehicle based at least in part on the information about the second vibrations that is modified.

7. The system of claim 6, wherein the sensing system is configured to monitor the changes in the baseline vibrations by identifying one or more of a changing frequency of one or more peaks in a frequency spectrum of the baseline vibrations or a changing amplitude of the one or more peaks in the frequency spectrum of the baseline vibrations.

8. The system of claim 6, wherein the sensing system is configured to distinguish between the second vibrations and the baseline vibrations based at least in part on times at which the baseline vibrations are generated.

9. The system of claim 6, wherein the control system is configured to introduce the baseline vibrations by automatically moving a weighted object portion of the control system relative to the surface above the fiber optic cable.

10. The system of claim 6, wherein the sensing system is configured to receive the information about the second vibrations from one or more sensors operably connected with the fiber optic cable.

11. A sensing system comprising:
one or more sensors configured to examine light traveling through a fiber optic cable extending along and beneath a route traveled by vehicles;
a control system configured to introduce baseline vibrations into the fiber optic cable by automatically imparting a force onto a surface of ground in which the fiber optic cable is buried;
one or more sensing processors configured to monitor changes in the baseline vibrations introduced into the fiber optic cable at designated times, the one or more sensing processors also configured to determine information about environmental conditions outside of the fiber optic cable based at least in part on the changes in the baseline vibrations that are monitored,
wherein the one or more sensing processors also are configured to monitor second vibrations generated by movement of a vehicle using the fiber optic cable, to determine information about the second vibrations, and to modify the information about the second vibrations by one or more of shifting a frequency of one or more peaks in a frequency spectrum of the second vibrations or changing an amplitude of the one or more peaks in the frequency spectrum of the second vibrations by an amount that matches the changes in the baseline vibrations, and
wherein the one or more sensing processors are configured to determine information about the vehicle based at least in part on the information about the second vibrations that is modified.

12. The system of claim 11, wherein the one or more sensing processors also are configured to monitor vibrations of interest generated by movement of an object of interest using the fiber optic cable, the one or more sensing processors are configured to modify the vibrations of interest based at least in part on the changes in the baseline vibrations that are monitored, and the one or more sensing processors are configured to identify information about the object of interest based at least in part on the vibrations of interest that are modified.

13. The system of claim 12, wherein the one or more sensing processors are configured to modify the vibrations of interest by one or more of shifting a frequency of one or more peaks in a frequency spectrum of the vibrations of interest or changing an amplitude of the one or more peaks in the frequency spectrum of the vibrations of interest.

14. The system of claim 13, wherein the one or more sensing processors are configured to modify the vibrations of interest by one or more of shifting the frequency of one or more peaks in the frequency spectrum of the vibrations of interest or changing the amplitude of the one or more peaks in the frequency spectrum of the vibrations of interest by an amount that matches the changes in the baseline vibrations.

* * * * *